(12) United States Patent
Carrel

(10) Patent No.: US 8,876,778 B2
(45) Date of Patent: Nov. 4, 2014

(54) INJECTION DEVICE WITH RETAINING MEANS ACTUATED BY NEEDLE SHIELD

(75) Inventor: Franck Carrel, Le Pont de Claix (FR)

(73) Assignee: Becton Dickinson France, Le Pont de Claix (FR)

( * ) Notice: Subject to any disclaimer, the term of this patent is extended or adjusted under 35 U.S.C. 154(b) by 711 days.

(21) Appl. No.: 13/120,973

(22) PCT Filed: Sep. 29, 2008

(86) PCT No.: PCT/IB2008/003281
§ 371 (c)(1),
(2), (4) Date: May 17, 2011

(87) PCT Pub. No.: WO2010/035058
PCT Pub. Date: Apr. 1, 2010

(65) Prior Publication Data
US 2011/0213312 A1 Sep. 1, 2011

(51) Int. Cl.
*A61M 5/32* (2006.01)
*A61M 5/20* (2006.01)

(52) U.S. Cl.
CPC ..... *A61M 5/2033* (2013.01); *A61M 2005/2073* (2013.01); *A61M 5/3202* (2013.01); *A61M 2005/206* (2013.01)
USPC .......................................... 604/192

(58) Field of Classification Search
CPC ................. A61M 2005/206; A61M 2205/581; A61M 5/2033; A61M 5/31511; A61M 5/3157; A61M 5/3287
USPC ......... 604/191, 192, 198, 110, 181, 135, 136, 604/187, 208, 218–231
See application file for complete search history.

(56) References Cited

U.S. PATENT DOCUMENTS

2006/0189938 A1* 8/2006 Hommann et al. ........... 604/137

FOREIGN PATENT DOCUMENTS

| WO | 01/93926 A2 | 12/2001 |
| WO | 03/013632 A2 | 2/2003 |
| WO | 2007/132353 A2 | 11/2007 |
| WO | 2009/019437 A1 | 2/2009 |

* cited by examiner

*Primary Examiner* — Kami A Bosworth
*Assistant Examiner* — Imani Hayman
(74) *Attorney, Agent, or Firm* — Hoffmann & Baron, LLP

(57) ABSTRACT

A device is presented for injection of a product into an injection site, comprising: a container provided with a needle, a housing receiving the container, and a needle shield releasably coupled with the container. The device also includes a retaining arrangement provided at or near the distal end of the device, designed for preventing the container from moving distally with respect to the housing until the needle shield is removed from the container.

7 Claims, 2 Drawing Sheets

INJECTION DEVICE WITH RETAINING MEANS ACTUATED BY NEEDLE SHIELD

Figure 1:
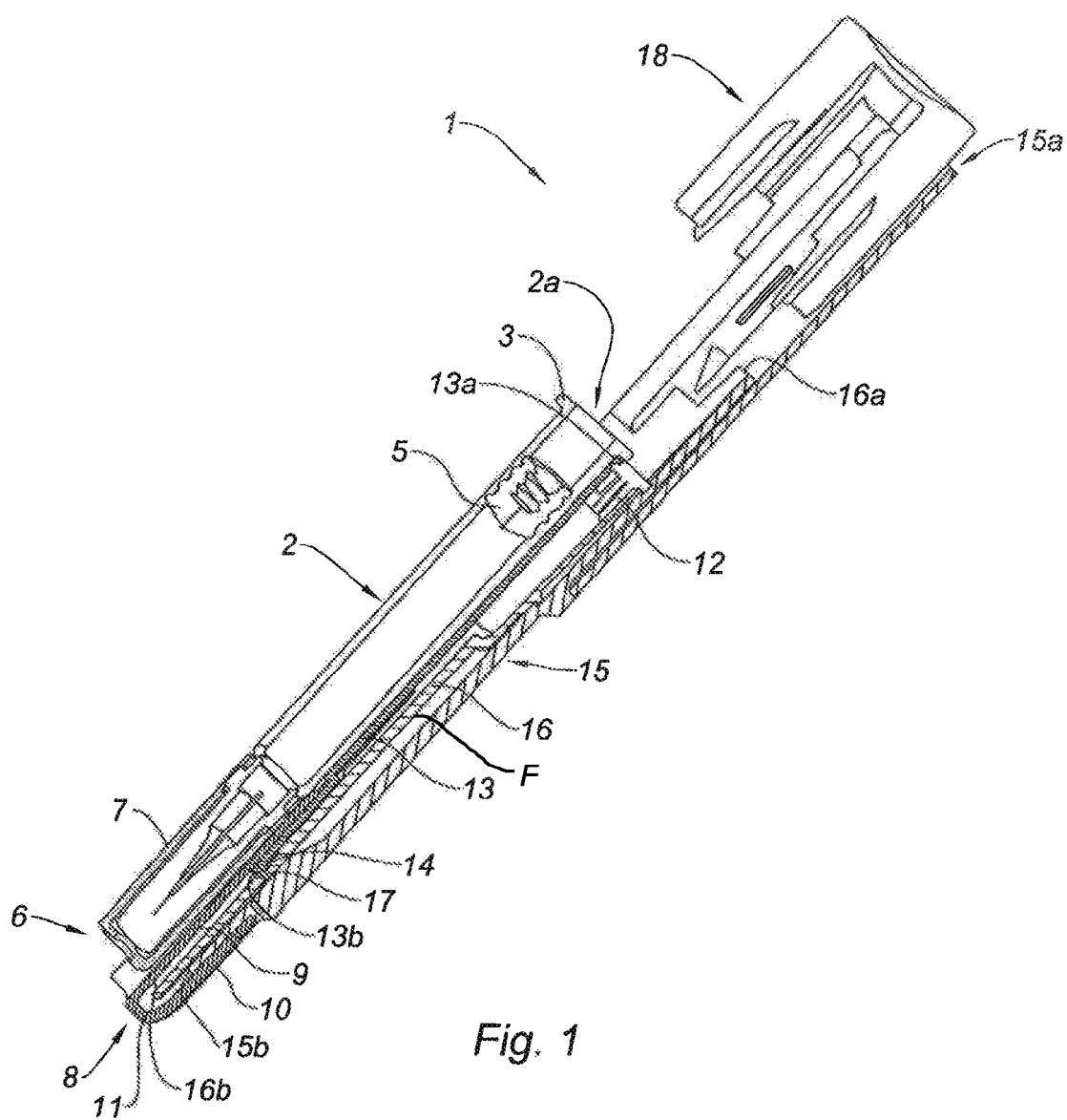

The present invention relates to a device for injection of a product in a very safe way, especially for self-injection.

In this application, the distal end of a component or of a device is to be understood as meaning the end furthest from the user's hand and the proximal end is to be understood as meaning the end closest to the user's hand. Likewise, in this application, the "distal direction" is to be understood as meaning the direction of injection, and the "proximal direction" is to be understood as meaning the opposite direction to the direction of injection.

Some illnesses necessitate regular injections of drugs or products, for instance on a daily basis. In order to simplify the treatment, some self-injectors have been provided in order to allow the patient to perform the injection on its own.

Of course, since the patient is usually neither a nurse nor an educated person in medical devices, such self-injectors must prove to be very simple to use and also very safe. In particular, the insertion of the needle must be performed at the right depth, the correct dose of product must be injected, that is to say a complete injection must be performed, and the injector must comprise a safety system to deactivate it after use before it is disposed of. Preferably, the needle should not be exposed, before and after use, in order to prevent any accidental needle-stick injury.

In general, such self-injectors are comprised within a housing receiving the container and injection means, thereby rendering the device easier to use for the patient/user.

The injection devices of the prior art are usually provided with needle shields that are made of rubber or elastomeric material in order to protect the needle prior to the use of the device. Thanks to the rubber or elastomeric material, the needle shield is usually coupled to the container comprising the product to be injected by friction forces. The user removes the needle shield from the container prior to use.

Nevertheless, because of the pulling force that needs to be exerted on the needle shield, at the time of its removal, it may happen that the container is also pulled distally and moves with respect of the other parts of the device, for example with respect to the housing. This has the drawback that the container may be removed from the device or that the container may me misplaced with respect to its normal initial position. This can lead to misuse of the device: for example, the needle may not be inserted at the correct insertion depth at the time of injection, or a wrong dose may be injected, or the safety system may not work properly at the end of injection.

The document WO2007/132353 describes some devices for autoinjection that comprise a needle shield to be removed prior to use of the device. In WO2007/132353, when the needle shield is removed, the container is prevented from moving with respect to the housing by retaining means that maintain the container fixed with respect to the housing, these retaining means being located proximate to the proximal end of the container. Moreover, the retaining means remain activated once the needle shield is removed, and the user must deactivate this retaining means before proceeding to the injection: this operation of deactivating the retaining means may be painful for the patient: for example, in the case of the device of WO2007/132353, the user needs to apply the device with a high force on his skin in oder to deactivate the retaining means.

It would therefore be of interest to provide an injection device that would prevent the container to move with respect to the housing when the needle shield is removed but that would not subsequently necessitate a painful step before use.

The present invention meets this need by proposing a device for injection of a product into an injection site, said device comprising retaining means for preventing the container to move with respect to the housing when the needle shield is removed, said retaining means being located near the distal end of the device. Moreover, in the device of the invention, the retaining means may be automatically deactivated at the end of removal of the needle shield, without any additional operation from the user.

The present invention relates to a device for injection of a product into an injection site, the product being carried by a container having an open proximal end and a substantially closed distal end carrying a needle to provide an outlet port for the product from the container, and a piston provided in the container and movable with respect to the container, the movement of the piston causing the product to be expelled from the container through the needle, said device comprising:

a housing receiving at least partly said container, said container being movable relative to said housing between an initial position, in which a tip of the needle does not extend beyond a distal end of said housing and an insertion position, distally spaced relative to said initial position, and in which the tip of the needle extends beyond said distal end of said housing, a needle shield releasably coupled with said container, for protecting said needle prior to use of the device, said device being characterized in that it further comprises:

retaining means provided at or near said distal end of said device, designed for preventing said container to move distally with respect to said housing until said needle shield is removed from said container.

Thanks to the presence of the retaining means near the distal end of the device of the invention, the container does not move with respect to the housing when the needle shield is removed prior to use: as a consequence, the removal of the needle shield has no impact on the quality of the injection.

In an embodiment of the invention, said retaining means comprise at least one flexible element, said flexible element being capable of deflecting from a stressed position, in which said flexible element prevents said container to move distally with respect to said housing, to a released position, in which said flexible element does not prevent said container to move distally with respect to said housing, removal of said needle shield from said container causing said flexible element to go from its stressed position to its released position.

In particular, the retaining means are automatically deactivated by the removal of the needle shield; the user does not need to perform an additional step in order to deactivate the retaining means after removal of the needle shield. Also, in the case of a device as described in WO2007/132353, the user does need to apply the device on the injection site with a high pressure in order to deactivate the retaining means.

In an embodiment of the invention, said needle shield comprises a pushing surface, said pushing surface being in contact with said flexible element prior to removal of said needle shield from said container, said pushing surface thereby forcing said flexible element in its stressed position prior to removal of said needle shield.

In an embodiment of the invention, said flexible element having a fixed part attached directly or indirectly to said container and a free part provided with a peg, said retaining means further comprise a recess located on said housing or on a part coupled to said housing, said peg being engaged into said recess when said flexible element is in its stressed position, said peg being disengaged from said recess when said flexible element is in its released position.

For example, the fixed part of the flexible element may be attached directly on the container by means of clips located on said flexible element grasping a flange of said container. Alternatively, a ring may be clipped on a flange of the container and the fixed part of the flexible element is attached to the ring: the fixed part of the flexible element is therefore indirectly attached to the container.

In an embodiment of the invention, said flexible element comprises a longitudinal leg, a proximal end of said longitudinal leg being attached to a proximal flange of said container by means of a ring coupled to said proximal flange, a distal end of said longitudinal leg being free and being provided with said peg.

In an embodiment of the invention, said device further comprises a safety shield, said safety shield receiving said container and being received within said housing, said safety shield being coupled to said housing at least when said container is in its initial position, part of said retaining means being located on an inner wall of said safety shield. For example, said safety shield is coupled to said housing by means of coupling means that maintain said safety shield fixed with respect to said housing at least when said container is in its initial position.

Such a safety shield may be designed for protecting the needle before use and after use, at the end of injection, in order to avoid accidental needlestick injuries. Such a safety shield may be coupled to the housing so that said safety shield is movable with respect to said housing when the container leaves its initial position, for example for the steps of insertion of the needle and injection. Such a safety shield is described in WO2007/132353.

In an embodiment of the invention, said pushing surface comprises a longitudinal wall of said needle shield, said longitudinal wall being located between said container and said flexible element and thereby forcing and engaging said peg into said recess prior to removal of said needle shield. In an embodiment of the invention, the needle shield comprises a rubber part at least partially enclosed by a rigid part and the longitudinal wall is part of said rigid part.

In an embodiment of the invention, the device further comprises automatic injection means and triggering means for activating said automatic injection means. Such a device is therefore very simple to use for the patient: the automatic injection means may comprise one or more helical spring pushing the piston distally at the time of injection and the triggering means may comprise a push button having means for freeing the helical spring(s) at the time of injection. Such automatic injections means together with corresponding triggering means are described in WO2007/13253.

Figure 2:
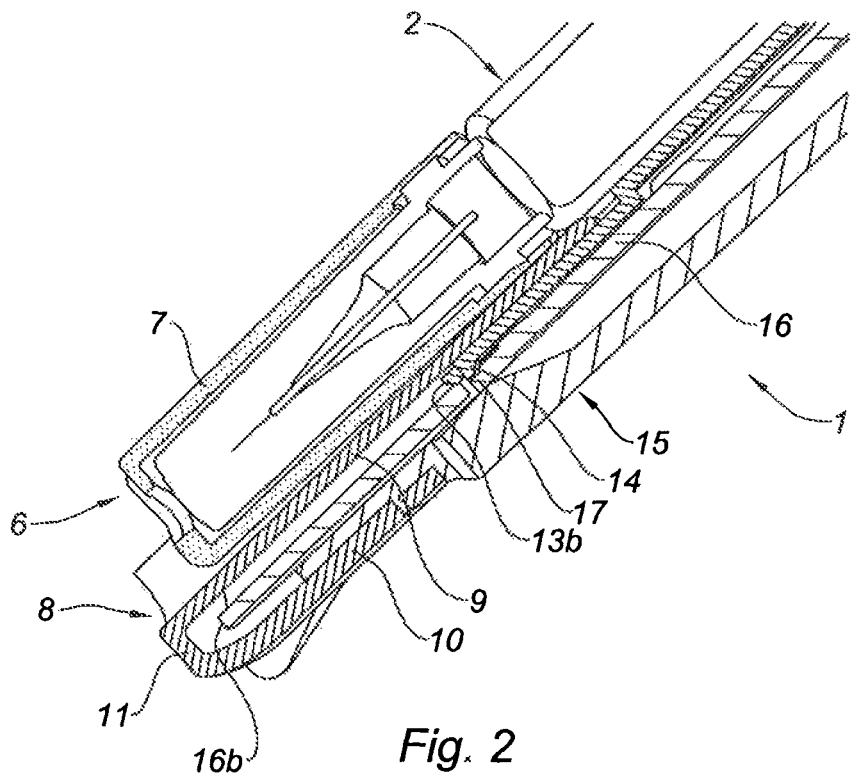
Figure 3:
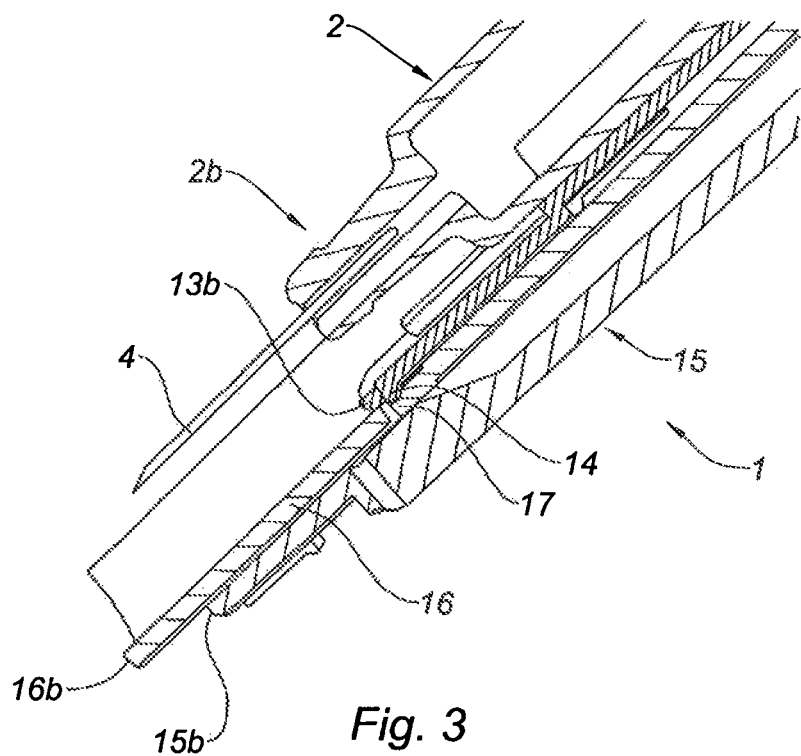

The device of the invention will now be further described in reference to the following description and attached drawings in which:

FIG. 1 is a partial longitudinal cross section view of an embodiment of the device of the invention prior to removal of the needle shield, FIG. 2 is a detailed view of the FIG. 1 showing the interaction between the element and the safety shield, FIG. 3 is a partial longitudinal cross section view of the device of FIGS. 1 and 2 after removal of the needle shield.

Referring now to the drawings, the present invention will now be described in detail. FIG. 1 shows a partial longitudinal cross section view of a device for injection of a product according to an embodiment of the present invention and generally designated by reference number 1. The device 1 of the invention comprises a container 2 carrying a product to be injected into an injection site. The container 2 has an open proximal end 2a provided with a flange 3 and a substantially closed distal end 2b bearing an injection needle 4 (see FIG. 3). The injection needle 4 is in fluid communication with the container 2 and provides an outlet port for the product from the container 2. A piston 5 is provided in the container 2 and movable with respect to the container 2: the movement of the piston 5 is intended to cause the product to be expelled from the container 2 through the needle 4. A piston rod, not shown, may cause the movement of the piston 5. As appears on FIG. 1, prior to the use of the device, a needle shield 6 is provided at the distal end 2b of the container 2 to cover and protect the needle 4 before use of the device 1. The needle shield 6 comprises a rubber part 7 which is coupled to the distal end 2b of the container 2 for example by friction forces. Alternatively, the needle shield may comprise an elastomeric material. The rubber part 7 of the needle shield 6 realises a tight sealing of the distal end 2b of the container 2.

On the example shown, the needle shield 6 further comprises a rigid part 8 enclosing the rubber part 7. The rigid part 8 has the global shape of a cap comprising an inner cylinder 9 and an outer cylinder 10, joined at their respective distal ends by a transversal wall 11. The inner cylinder 9 forms a longitudinal wall enclosing the rubber part 7 of the needles shield 6. The rigid part 8 and the rubber part 7 of the needle shield 6 are permanently fixed to each other.

A ring 12 receiving the proximal part of the container 2 is fixed to the flange 3 of the container 2, for example by means of clips (not shown).

Between the container 2 and the ring 12, is located a flexible element F extending in the distal direction under the shape of a longitudinal leg 13. The proximal end 13a of said longitudinal leg 13 is fixed to said container 2, in particular to the flange 3 of said container 2, by the intermediate of said ring 12. The distal end 13b of said longitudinal leg 9 is free and is provided with a peg 14.

The device 1 of FIGS. 1-3 further comprises a housing 15 receiving at least partially said container 2. On the example shown, the housing 15 has a general tubular shape with an open proximal end 15a and an open distal 15b. On the FIGS. 1-3, the device 1 is shown prior use and the container 2 is in a initial position with respect to the housing 15, ie the container 2 is in a position in which the tip of the needle 4 does not extend beyond the distal end 15b of the housing 15. The container 2 is nevertheless movable with respect to the housing 15 to an insertion position, in which the tip of the needle 4 extends beyond the distal end 15b of the housing: in such an insertion position (not shown), the injection may be completed. Such container and housing, movable with respect to each other, are described in WO2007/13253.

In the prior use position as shown on FIGS. 1 and 2, the rigid part 8 of the needle shield may be releasably coupled to the distal end 15b of the housing 15. As shown on FIGS. 1 and 2, in the before use position of the device 1, the inner cylinder 9 of the rigid part 8 is located between the outer wall of the rubber part 7 of the needle shield 6 and the inner wall of the longitudinal leg 13.

The device 1 of FIGS. 1-3 further comprises a safety shield 16 receiving at least partially said container 2. On the example shown, the safety shield 16 has a general tubular shape with an open proximal end 16a and an open distal end 16b. In its distal region, the safety shield 16 is provided on its inner wall with a recess 17. The safety shield 16 is received within the housing 15 and coupled to said housing at least when said container 2 is in its initial position.

The safety shield 16 may be movable with respect to said container 2 between a protection position, in which a tip of said needle 4 does not extend beyond the distal end 16b of said safety shield 16 (as shown on FIGS. 1-3), and an insertion position, in which the tip of the needle 4 extends beyond said distal end 16b of said safety shield 16. The safety shield 16 may also be designed for covering the needle 4 at the end of the injection, in order to avoid accidental needlestick injuries for the user. Such safety shields are described in WO2007/13253.

Moreover, as shown on FIGS. 1 and 2, in the before use position of the device 1, the distal end 13b of the longitudinal leg 13 is located between the wall of the inner cylinder 9 and the wall of the safety shield 16. Moreover, in this position, the wall of the inner cylinder 9 constitutes a pushing surface that is in contact with, and forces, the distal end 13b of the longitudinal leg 13 in its stressed position, thereby causing the peg 14 to be engaged in the recess 17 of the safety shield 16.

When the user decides to proceed with the administration of the product, he pulls on the rigid part 8 of the needle shield 6, thereby causing the rubber part 7 of the needle shield 6 to be removed from the container 2.

During the step of removal of the needle shield 6, the container 2 does not move proximally: indeed, during this step, the peg 14 is engaged in the recess 17 by the longitudinal wall of the inner cylinder 9 forcing the distal end 13b of the longitudinal leg 13 in its stressed position. As a consequence, the container 2, to which the longitudinal leg 13 is fixed, is prevented to move with respect to the safety shield 16.

Once the needle shield 6 has been removed, as shown on FIG. 3, the wall of the inner cylinder 9 of the rigid part 8 of the needle shield 6 no longer forces the distal end 13b of the longitudinal leg 13 in its deflected or stressed position. As a consequence, as shown on FIG. 3, the distal end 13b of the longitudinal leg 13 comes back to its non deflected, i.e., released, position and the peg 14 disengages from the recess 17 of the safety shield 16.

The non-deflected and released position of the distal end 13b of the longitudinal leg 13 will therefore allow the container 2 to move distally in order to realise the injection upon further action of the user in order to initiate the insertion of the needle and the injection.

As appears clearly from the description above and from the figures, the longitudinal wall of the inner cylinder 9, the flexible longitudinal leg 13 in its stressed position, and in particular the peg 14, together with the recess 17 of the safety shield 16 are located at the distal end of the device 1 and they act as retaining means preventing the container 2 to move distally with respect to the housing 15, which is coupled to the safety shield 16, before the removal of the needle shield 6. The removal of the needle shield 6 from the container 2 causes the longitudinal leg 13 to go from its stressed position to its released position. In the released position of the longitudinal leg 13, the peg 14 disengages from the recess 17 of the safety shield 16, and the longitudinal leg 13 does not prevent anymore the container 2 to move distally with respect to the housing 15, which is coupled to the safety shield 16; in consequence, in the device 1 of the invention, the retaining means are automatically released by simply removing the needle shield 6 and the user does not have to perform an additional potentially painful operation in order to release these retaining means before initiating the insertion of the needle and the injection.

In an embodiment not shown, the device may comprise automatic injections, for example under the shape of one or more helical springs intended to push distally the piston. 5. The device may further comprise triggering means, such as a push button similar to the push button 18 shown on FIG. 1. The user may then trigger the device 1, by means of a push button, and free the automatic injection means to realise the injection: such a push button and automatic injections means usable in the device of the invention are described in WO2007/13253.

The device of the invention is very easy to use and very safe. In particular, with the injection device, the risk that the container be removed from the device at the time the needle shield is removed from the injection device is avoided thanks to retaining means. In particular, the retaining means may be automatically deactivated after removal of the needle shield, without requiring additional operation by the user.

What is claimed is:

1. A device for injection of a product into an injection site, the product being carried by a container having an open proximal end and a substantially closed distal end carrying a needle to provide an outlet port for the product from the container, and a piston provided in the container and movable with respect to the container, the movement of the piston causing the product to be expelled from the container through the needle, said device comprising:
   a housing receiving at least partly said container, said container being movable relative to said housing between an initial position, in which a tip of the needle does not extend beyond a distal end of said housing and an insertion position, distally spaced relative to said initial position, and in which the tip of the needle extends beyond said distal end of said housing,
   a needle shield releasably coupled with said container, for protecting said needle prior to use of the device, and,
   retaining means provided at or near said distal end of said device, designed for preventing said container from moving distally with respect to said housing until said needle shield is removed from said container so as to be completely separated from the device,
   wherein, said retaining means comprise at least one flexible element, said flexible element being capable of deflecting from a stressed position, in which said flexible element prevents said container to move distally with respect to said housing, to a released position, in which said flexible element does not prevent said container to move distally with respect to said housing, removal of said needle shield from said container causing said flexible element to go from its stressed position to its released position,
   wherein, said needle shield comprises a pushing surface, said pushing surface being in contact with said flexible element prior to removal of said needle shield from said container, said pushing surface thereby forcing said flexible element in its stressed position prior to removal of said needle shield, and
   wherein, prior to removal of said needle shield from said container, said pushing surface being in contact with said flexible element near said distal end of said device.

2. The device according to claim 1, wherein said flexible element having a fixed part attached directly or indirectly to said container and a free part provided with a peg, said retaining means further comprise a recess located on said housing or on a part coupled to said housing, said peg being engaged into said recess when said flexible element is in its stressed position, said peg being disengaged from said recess when said flexible element is in its released position.

3. The device according to claim 2, wherein said flexible element comprises a longitudinal leg, a proximal end of said longitudinal leg being attached to a proximal flange of said container by means of a ring coupled to said proximal flange, a distal end of said longitudinal leg being free and being provided with said peg.

4. The device according to claim 2, wherein said pushing surface comprises a longitudinal wall of said needle shield, said longitudinal wall being located between said container and said flexible element and thereby forcing and engaging said peg into said recess prior to removal of said needle shield.

5. The device according to claim 4, wherein said needle shield comprises a rubber part at least partially enclosed by a rigid part, said longitudinal wall being part of said rigid part.

6. The device according to claim 1, wherein said device further comprises a safety shield, said safety shield receiving said container and being received within said housing, said safety shield being coupled to said housing at least when said container is in its initial position, part of said retaining means being located on an inner wall of said safety shield.

7. The device according to claim 1, wherein said device further comprises automatic injection means and triggering means for activating said automatic injection means.

\* \* \* \* \*